US010088227B2

(12) United States Patent
Bowdish (10) Patent No.: US 10,088,227 B2
(45) Date of Patent: Oct. 2, 2018

(54) SYSTEMS AND METHODS FOR A WIDE RANGE CRYOPROCESSOR

(71) Applicant: Boyd Bowdish, Los Gatos, CA (US)

(72) Inventor: Boyd Bowdish, Los Gatos, CA (US)

(73) Assignee: Reflect Scientific Inc., Orem, UT (US)

( * ) Notice: Subject to any disclaimer, the term of this patent is extended or adjusted under 35 U.S.C. 154(b) by 519 days.

(21) Appl. No.: 14/613,702

(22) Filed: Feb. 4, 2015

(65) Prior Publication Data

US 2016/0223248 A1 Aug. 4, 2016

(51) Int. Cl.
| | | |
|---|---|---|
| *F25D 13/04* | (2006.01) | |
| *F25D 29/00* | (2006.01) | |
| *F25D 3/10* | (2006.01) | |
| *F25D 13/06* | (2006.01) | |
| *F25D 31/00* | (2006.01) | |
| *A01N 1/02* | (2006.01) | |
| *B01L 7/00* | (2006.01) | |

(52) U.S. Cl.
CPC ......... *F25D 29/001* (2013.01); *A01N 1/0257* (2013.01); *F25D 3/10* (2013.01); *F25D 13/067* (2013.01); *F25D 31/005* (2013.01); *B01L 7/50* (2013.01)

(58) Field of Classification Search
CPC .......... F25D 2/001; F25D 3/10; F25D 31/005; A01N 1/0257
See application file for complete search history.

(56) References Cited

U.S. PATENT DOCUMENTS

| | | | | |
|---|---|---|---|---|
| 4,233,817 A | * | 11/1980 | Toth | ............ F25D 3/10 165/288 |
| 5,320,167 A | * | 6/1994 | Johnson | ........... F25D 29/001 165/61 |
| 5,730,216 A | * | 3/1998 | Viegas | ............ F25D 3/10 165/233 |
| 7,621,148 B1 | * | 11/2009 | Dain | ........... F25D 23/063 220/592.01 |
| 2009/0113899 A1 | * | 5/2009 | Dain | ............ F25D 11/04 62/48.1 |

* cited by examiner

*Primary Examiner* — Orlando E Aviles Bosques
(74) *Attorney, Agent, or Firm* — Tran & Associates (57) ABSTRACT

A wide range cryoprocessor is disclosed which allows for the freezing and the thawing of bio-samples in a single unit, and at controlled rates. Improvements have been made to enhance freezing performance by switching the liquid nitrogen flow control to the extreme downstream side. A second feature has been added to the cryoprocessor, capability to raise the temperature of a sample environment to a user's requirements through the use of a flashed cryogen and heating that gas flow for use in the heat exchanger on the freezer.

8 Claims, 5 Drawing Sheets

FIG. 5 raising a temperature of a sample environment to a predetermined requirement through a flashed cryogen heating gas flow for use in a heat exchanger on a freezer running a cooling cycle by opening an inlet valve and using a downstream gas control valve to meter a flow of cryogen through a heat exchanger and pressure wave control by constricting an inner diameter of a coil of the heat exchanger, wherein for every third opening of an inlet valve, opening a cooling control valve to reduce induced pressure in the coil providing a pressure relief valve for the coil

SYSTEMS AND METHODS FOR A WIDE RANGE CRYOPROCESSOR

BACKGROUND

In the field of cryopreservation of biological proteins and other tissue or cell materials there are two needs that are addressed here. The first is to speed up the cool down of the ULT freezer while using less liquid nitrogen. Secondly, there is a need for the cryopreserved samples to be reheated (thawed) in a controlled manner while reducing the human intervention into the process. To improve on the cryogenic ultra low freezer cool-down (U.S. Pat. No. 7,823,394, U.S. Pat. No. 8,424,317) process and novel design has been developed. This design fully uses both the latent heat of vaporization and of the sensible energy potential of the cryogen fuel. The liquid nitrogen flow in traditional cryogenic freezers is controlled by an array of either vacuum insulated or foam insulated valves at the beginning of the liquid flow process. This is an inefficient way of introducing saturated liquid to the cooling process. The closer to saturated liquid nitrogen, the larger DeltaT is present on the heat exchange portion of the cooling process (U.S. Pat. No. 7,823,394, U.S. Pat. No. 7,621,148). These freezer designs are run open loop presenting a little backpressure to the flow of cryogen. The boiled off gas from the vaporization of the cryogen is pushed out of the system via the incoming pressure of the cryogen. In this application, the control of the liquid cryogen gas is controlled on the exit end of the cryogen flow path. This technique called "Pressure Wave Flow Control" is a closed loop system. The output controlled by use of a control valve on the exit of the system. Currently, the protein product/samples are frozen to typically –85 C or –150 C to preserve the samples while they are in WIP (work in process) waiting for the need to thaw and continue manufacturing of the biopharmaceutical. The freezing portion of this is conducted in several different packages or containers. The thawing is then conducted in a separate system. This exposes the package or container to very rapidly heating to ambient temperatures. This exposure has been shown in the past to introduce mechanical stress into the packaging be it either from reintroduction into a larger scale freezing room or into the thaw process of the protocol. This mechanical stress has led to packages and containers to demonstrate splitting, cracking and to compromise the sterile solution inside. This is unacceptable and leads to extensive cleanup and bio hazard to the technical staff performing the cross-over operations. It also wastes valuable product. This can severely hinder public response to epidemic medical challenges.

SUMMARY

In one aspect, systems and method for controlling a cryoprocessor includes switching a liquid nitrogen flow control to a downstream side of a payload bay heat exchanger to enhance freezing performance; raising a temperature of a sample environment to a predetermined requirement through a flashed cryogen and heating gas flow for use in a heat exchanger on a freezer; and running a cooling cycle by opening an inlet valve and using a downstream gas control valve to meter a flow of cryogen through a heat exchanger and pressure wave control.

In another aspect, a wide range cryoprocessor allows for the freezing and the thawing of bio-samples in a single unit, and at controlled rates. Freezing performance is improved by switching the liquid nitrogen flow control to the extreme downstream side. A second feature has been added to the cryoprocessor, capability to raise the temperature of a sample environment to a user's requirements through the use of a flashed cryogen and heating that gas flow for use in the heat exchanger on the freezer. A second heating technique is to place quartz lamps between the payload bay and the inner wall of the insulating shell. Flashed nitrogen gas is used in the coils to aid in temperature uniformity.

Implementations of the system may include one or more of the following. One embodiment uses two interconnected sub systems. The first is using a "Pressure Wave Control (PWC)" of the cryogen in a freezing device. The other is to use the cryogen as a carrier gas, which is heated and passed through the heat exchange coils and/or additional coils on the exterior bottom of the payload bay, to raise the temperature of the environment inside the payload bay, thus warming the contents at a controlled rate. Control of the warming process can be controlled either by temperature sensors in the payload bay or by a secondary technique such as a thermocouple in alcohol that is located in the payload bay. The PWC is a technique in which the introduced supply of cryogen material/liquids are gated by the high pressure of the liquid/gas (mixed media) downstream of the liquid source. The pressure of the downstream gas can be as high as 150 PSI where the source liquid is typically at 22 PSI. This higher pressure is developed by the introduction of heat into the cryogen flow from the payload bay. This heat removal from the payload bay thus lowers the temperature in the payload bay which reduces the product temperature in the payload bay. A valve is placed at the output of the coil assembly of the payload bay. This valve is controlled by the need to reach an internal temperature. As the process lowers in temperature a PID algorithm takes control of the flow, open and closing the exit valve to allow for a smooth controlled response to requested internal temperature. Two temperature sensors are used. One is the control thermocouple. This sensor is the information sent to the control network of what the actual temperature is in the payload bay. The second thermocouple is a lower limit sensor and is located at the bottom of the payload bay. This data is used as a safety device so the in the event of a temperature run-away, there is a back-up valve to stop the flow of cryogen and to keep the freezer cold. The term Pressure Wave Control is defined by the control constriction of the inner diameter of the coil of the heat exchanger. As the cooler, lower pressure liquid makes its way through the coil, it is warmed from the residual heat inside the payload bay. Through conduction, radiation and convection heat transfer actions in the payload bay, thermal energy is pulled from the payload bay and exchanged with the liquid/gas in the coils. The longer the gas in available the more of the cryogens sensible heat transfer properties are taking advantage of for removing heat from the payload. Also by using PWC, the likely hood of a cryogen liquid exiting the system as a cryogen is eliminated by using the higher pressure gas to block the coil passage way by ever decreasing the internal diameter for the coil. This gives the liquid no chance to move downstream, hence being available longer in the coil. This action raises the efficiency of the fuel use of the freezer. The second subsystem allows for the thawing of the product in the payload bay by using one of several possible processes. In one embodiment, the cryogen liquid that was being used to cool the freezer is plumbed to flow backwards through the payload heat exchanger. A set of resistive heaters are used on a vaporizer assembly located at the exit of the cooling plumbing. Inlet gas temperatures are compared with the internal thermocouples and an appropriate amount of heat is applied to the process. At this point, vaporized gas is also plumbed into the payload bay itself through the freezers patented purge ports. The pressure in the payload bay is maintained at 0.5 psi via a pressure relief valve connected to the payload bay. This pressure relief valve is used during the cooling phase to make certain that the payload bay pressure with vaporized nitrogen gas. This slight positive pressure is well within the operating limits of the system. As the payload bay heats up, a PID circuit controls the heaters for the now inlet gas. The use of cryogens in this embodiment is to help in preventing water vapor buildup in the payload bay, adding the time and expense of the operation. It is projected that the GN2 use rate will be about 300 SFPH. In another embodiment of the heating process, ambient air is used as the heating media. Room air is pumped into the system by an external source at the same rate as used the inert gas embodiment, 300 SCFH. An additional difference is that incoming air will need to be processed in a way as to remove all water vapor from the incoming air. This promotes a minimum of ice buildup during the thaw. With a dry environment, condensation will be very limited. In another embodiment, quartz lamps are installed to the external portions of the payload bay. The quartz lamps are then used to heat the surfaces of the payload bay while at the same time inert gas is flowed into the payload bay to setup a turbulent flow of gas around the product in the payload bay. The power to the quartz lamps is control by the thermocouples located in the freezer. An alternate thermal sensor in the payload bay can also be used to control the thawing cycle.

Advantages of the preferred embodiment may include one or more of the following. The application combines both freezing and thawing into one single, portable if desired, system. Samples are placed in the device, frozen to the desired temperature and when required can be thawed to a desired temperature at a rate of 1 C per minute. With the device fitted with this hybrid technique, cool-downs and open/close events are improved in regards to heat removal and cryogen efficacy.

DETAILED DESCRIPTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

This invention now will be described more fully hereinafter with reference to the accompanying drawings, in which exemplary embodiments are shown. Various embodiments are now described with reference to the drawings, wherein such as reference numerals are used to refer to such as elements throughout. In the following description, for purposes of explanation, numerous specific details are set forth in order to provide a thorough understanding of one or more embodiments. It may be evident, however, that such embodiment(s) may be practiced without these specific details. In other instances, well-known structures and devices are shown in block diagram form in order to facilitate describing one or more embodiments.

This invention may, however, be embodied in many different forms and should not be construed as limited to the embodiments set forth herein. These embodiments are provided so that this disclosure will be thorough and complete and will fully convey the scope of the invention to those of ordinary skill in the art. Moreover, all statements herein reciting embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and the such as represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular named manufacturer.

Figure 1:
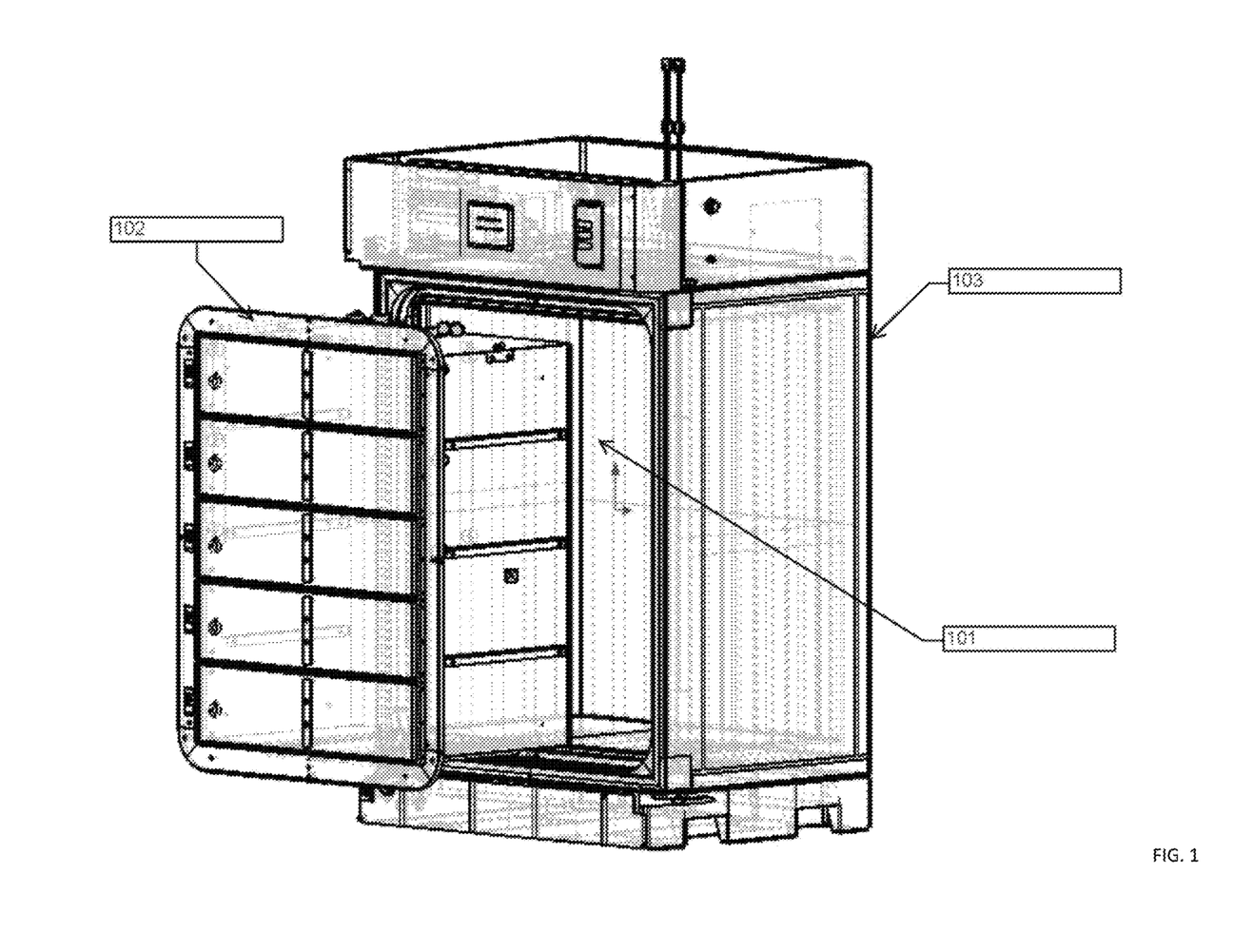
FIG. 1 shows an exemplary view of a wide range cryoprocessor.

FIG. 1 demonstrates the wide range cryoprocessor, 103. It shows a payload bay and the interstitial area, 101, used to house the heat exchanger coil that cool and heat the product in the payload bay, The coil wraps around the payload bay, 102, in a back and forth design with dual circular coils on the top of the payload bay, such as those taught by U.S. Pat. No. 7,621,148 commonly-owned by the assignee of the present invention and whose content is incorporated by reference. The inner doors are a component of the thermal insulation, U.S. Pat. No. 7,823,394 and U.S. Pat. No. 8,434,317 (commonly-owned by the assignee of the present invention and whose content is incorporated by reference), which allows for the wide temperature range and controllability of the cryoprocessor. In one embodiment, the freezer can achieve and maintain a set point and maintain it to within 1 C, for as long as there is liquid. In the heating cycle the same warming rate is achieved. The cryoprocessors can be vacuum insulated machines that process materials at the lowest total cost of any machine. The cryoprocessors are capable of automatically cycling payloads between the temperature limits of −300 and +320. Payload temperature is reduced by use of an internal heat exchanger to eliminate thermal shock that is possible and probable with spray bar machines. Integral heating elements make it possible to temper items in the machine as part of the automatic cycle. A microprocessor based industrial grade control is provided for programming, storage, and execution of complex time/temperature profiles. The system is capable of unattended running for periods of several days.

Figure 2:
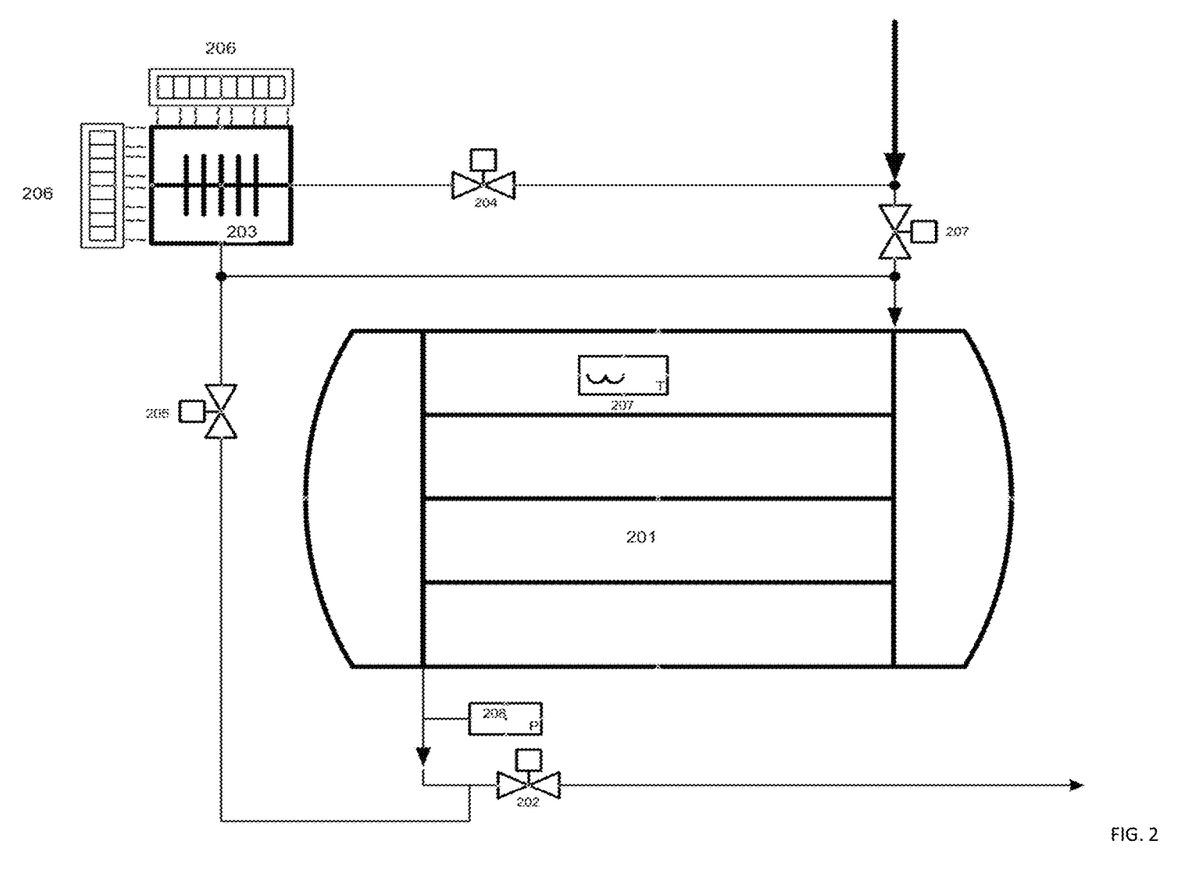
FIG. 2 shows an exemplary flow diagram for temperature control using heated gas with recycle circuit.

FIG. 2 demonstrates one embodiment of the wide range cryoprocessor with a recycle circuit of the heated nitrogen gas. The flow diagram includes temperature control using heated gas with recycle circuit. To cool the freezer, valve 207 is opened along with control valve 202. Control valve 202 is a proportioning gas valve. The cooling process uses a pressure wave scheme in which the flow of liquid nitrogen is gated by the warmer gas downstream. When liquid nitrogen is needed as sensed by thermocouple 207, the control valve 202 is opened.

Figure 3:
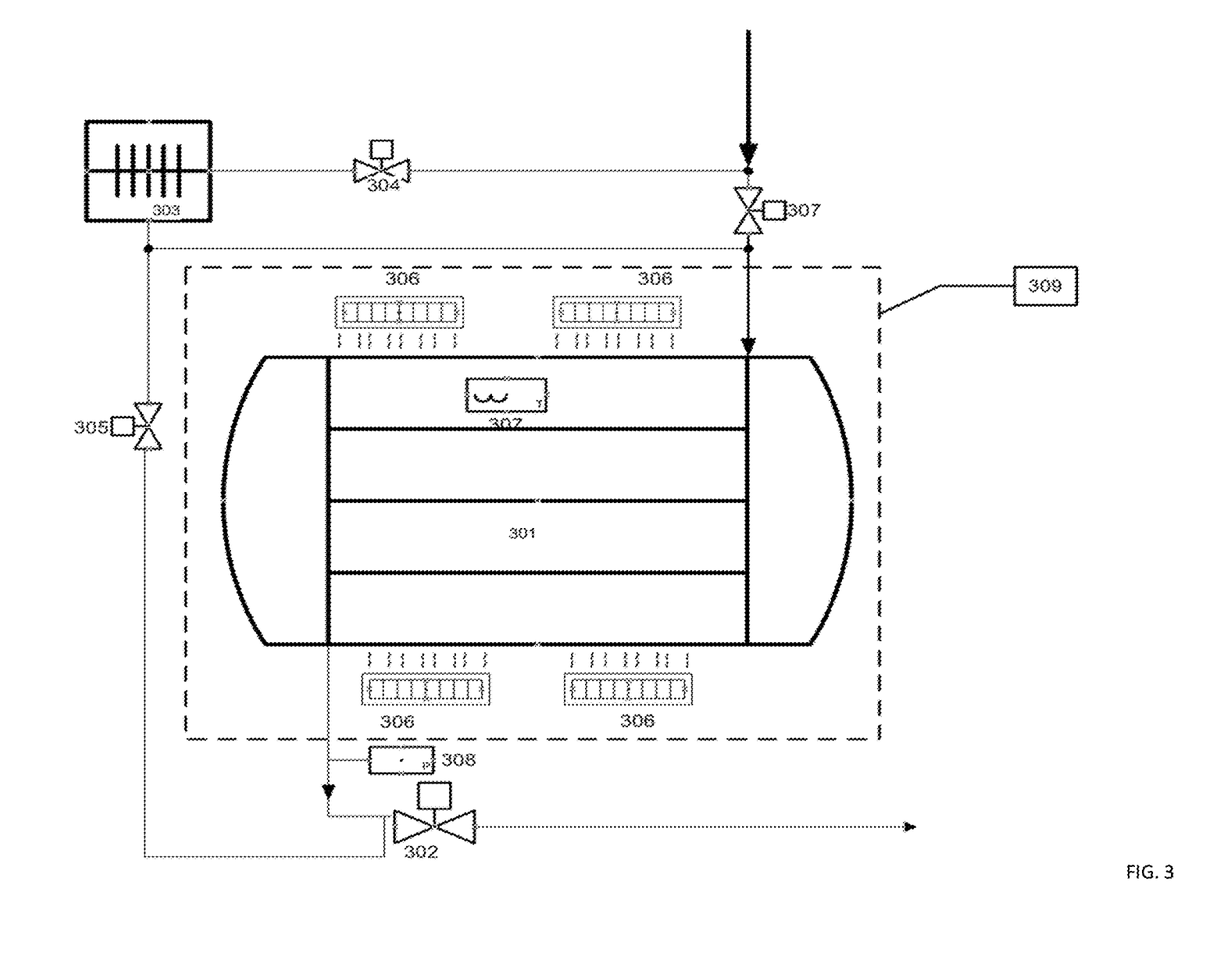
FIG. 3 shows an exemplary flow diagram of temperature control using quartz lamps heaters.
Figure 4:
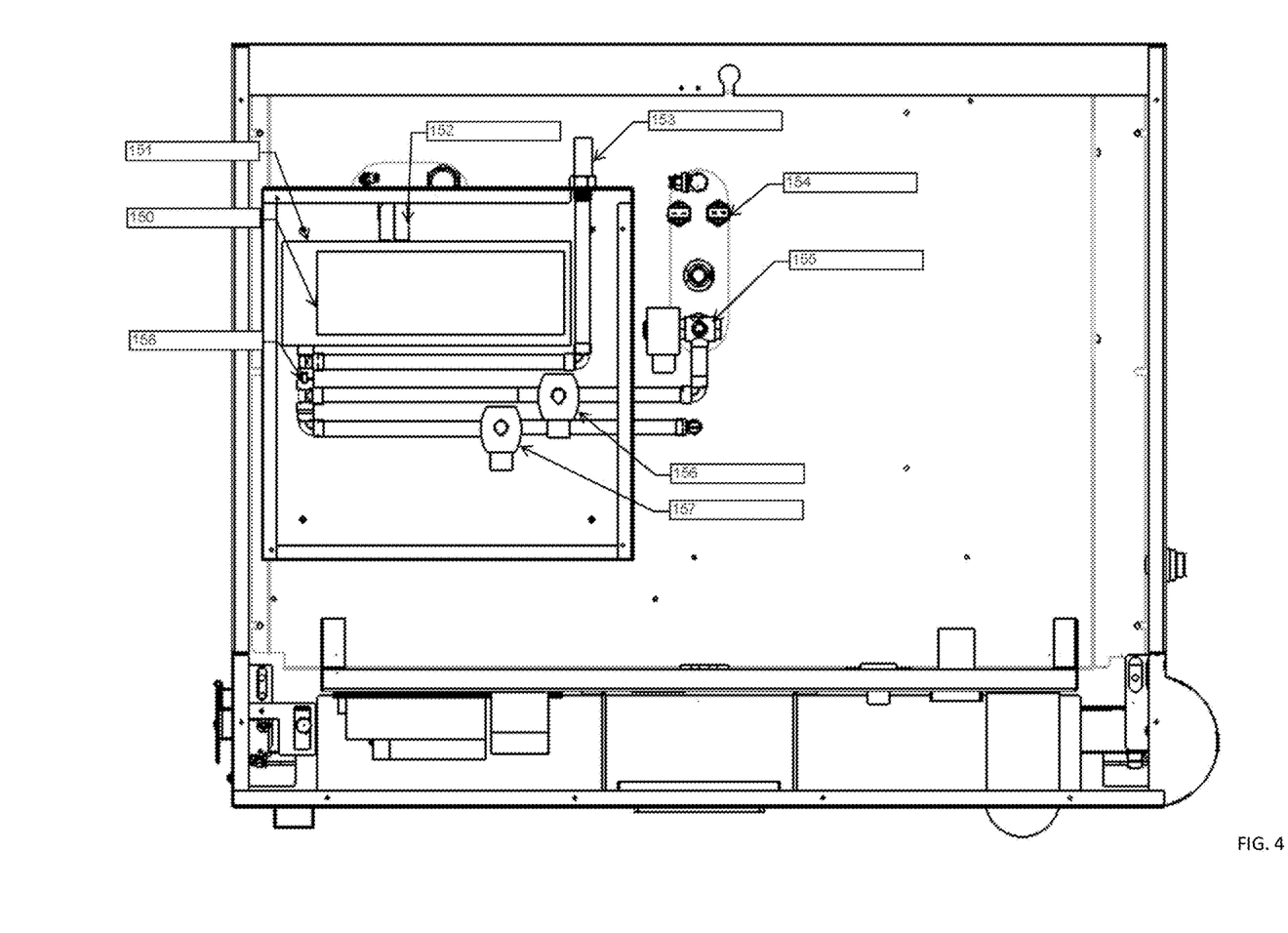
FIG. 4 shows an exemplary top view of cryoprocessor-flow path and
FIG. 5 shows a method for cryogenic control.
Figure 5:
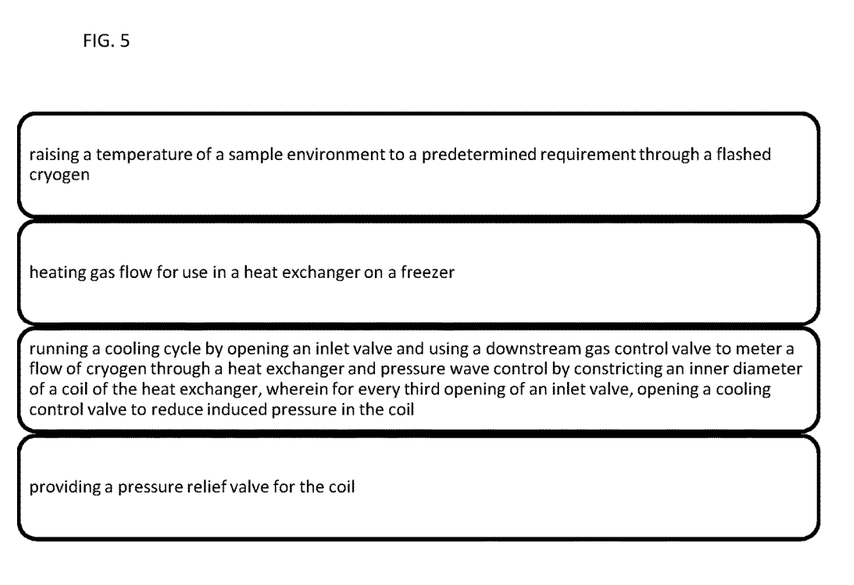

FIG. 3 shows a second embodiment of a wide range cryoprocessor using quartz lamps heaters. In this application the cooling cycle is run the same as FIG. 2 by opening inlet valve 307 and using the gas control valve 302 to meter the flow of cryogen through the heat exchanger. The difference is in the heat cycle. In this embodiment, 306 quartz lamps are installed so that they focus heat into the payload bay bottom section while gaseous nitrogen, which has gone through the process of vaporization, is flowed, unheated, through the coils of the cryoprocessor in which to have better control over temperature uniformity. In some instances it will be desired to have a high rate of rise with little concern of temperature uniformity of the product in the payload bay. Significantly higher heat loads can be applied with the use of quartz lamps. The gas is used to help with energy transfer to the top of the payload bay. As shown in FIG. 4, the addition of new LN2 into the gas phase flow is dependent on the pressure. The same algorithm is used to monitor rate of rise. By pulsing the quartz lamps and flowing gaseous nitrogen through the coil of the heat exchanger the payload bay is controlled to a desired higher temperature. The quartz lamps are installed in the interstitial area between the payload bay and inner wall of the outer insulating shell. The maximum temperature of the payload bay during the heating cycle is 110 C. The insulating shell will provide significant retention of the heat being applied to the payload bay. This available insulation will aid in the temperature uniformity of the heating cycle.

FIG. 4 shows an exemplary top view of the cryoprocessor. The cryogen flow path starts from a liquid nitrogen bulk supply which is connected at 155. The liquid then flows through the coil installed on the payload bay only if the heating control valve, 156, is open, the cooling control valve 157 is closed and inlet control valve 155 is open. The flow of low pressure liquid, below 90 psi, is gated by the warmer hence higher pressure gas in the coil. The higher pressure gas is formed by the vaporization of the cryogen in the coil by the payload bay heat load. The pressure delta between inlet and control valves can be as high as 150 psi which is regulated by the cracking pressure of pressure relief valve 153. Typically valve 153 does not come into play, as the pressure is regulated by the heat removal demands from the payload bay. This technique has been named Pressure Wave Control. This technique, PWC, fully utilizes the enthalpatic potential of the cryogen thus lowering liquid requirements to cool the payload bay. The temperature maintenance control algorithm uses a programmable logic controller, PLC. That is, the system compares the temperature of the payload bay via thermocouple 154, the users desired temperature, SP, and the outlet temperature, 158, to engage a PID routine that opens and closes the cooling control and the inlet control valve. The desired temperature deviation in a stable cooling condition will be +/−1 C. The output gas of the coil is transported through the payload bay exit tunnel, 152, and fitted directly to the Vaporizer coil pack, 151. The PLC monitors the outlet gas temperature and applies as much of its 1200 watt resistive element heater, 150, to the Vaporizer coil so that the outlet gas that flows though cooling control valve 157 is at ambient temperature. This exhaust will be plumbed to an exterior location for return to the external atmosphere. Thus, the technique of using a renewable resource as a fuel performs better than standard freezing techniques.

When the cooling control valve, 157 closes, the higher pressure in the vaporizer acts as an extreme deterrent for colder liquid cryogen flow at the inlet. This latent energy during the timeframe of rest, acts as a continuing cooler so that the overall payload bay remains in a very stable condition. In the heat cycle the material in the payload is required to be heated at a very specific rate of rise, +/−1 C per minute. To raise the temperature in the coils/payload by using vapor from 151 using its 1200 watt heating capability, 150. The data from the temp sensor, 158, working a duplicate algorithm with the PLC, raises the payload bay temperature by redirecting heated gaseous nitrogen through the coil located on the payload bay. Engaging the heat cycle closes cooling control valve 157, opens heating control valve 156 and closes the inlet valve 155. The PLC monitors the temperature ramp rate and when the rate of rise slows lower than the selected it is assumed that the flow of high pressure gas in the coils has come to equilibrium. At this point the algorithm will open inlet valve 155 for a time frame of between 0.5-5 seconds letting gaseous boil off from the liquid supply transfer system. Be it either foam insulated pipe or vacuum insulated piping. No matter the design of the transfer piping, the system takes advantage the natural occurring boil off which is then typically at an elevated temperature. The introduction of new pressurized gas then forces gas flow through the system to be reheated and returned to the process. Every third opening of the inlet valve 155, the algorithm opens the cooling control valve 157 for between 0.5 and 5 seconds to reduce the induced pressure in the coil. The coil is also monitored by pressure relief valve 153 making certain the pressure in the coil never exceeds 150 psi. The flow of heated gas into the coil of the heat exchanger/payload bay is monitored and compared by the PLC. Engaging a PID circuit that controls the timing and requirements for heat and taking the appropriate actions to maintain the rate of rise a desired pace. When the desired payload bay temperature as monitored by thermocouple 154, the PLC closes all valves and indicates that the cycle is complete.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present invention have been described above, it should be understood that they have been presented by way of example only, and not of limitation. The various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the such as; the term "example" is used to provide exemplary instances of the item in discussion, not an exhaustive or limiting list thereof; the terms "a" or an should be read as meaning "at least one," one or more or the such as; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Hence, where this document refers to technologies that would be apparent or known to one of ordinary skill in the art, such technologies encompass those apparent or known to the skilled artisan now or at any time in the future.

A group of items linked with the conjunction and should not be read as requiring that each and every one of those items be present in the grouping, but rather should be read as "and/or" unless expressly stated otherwise. Similarly, a group of items linked with the conjunction or should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to or other such as" phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for controlling a cryoprocessor, comprising:
   providing a pressure relief valve in the cryprocessor;
   operating the cryoprocessor in a cooling cycle for freezing an article within a sample environment, comprising:
      opening an inlet valve;
      allowing flow of a cryogen from a bulk supply into a coil heat exchanger of the cryprocessor via the inlet valve;
      using a cooling control valve downstream of the coil heat exchanger to meter the flow of the cryogen through the coil heat exchanger, thereby performing a pressure wave control by constricting an inner diameter of the coil heat exchanger;
      wherein by performing the cooling cycle, the cryogen is heated and changes to a gas;
   operating the cryoprocessor in a heating cycle for thawing the article within the sample environment, comprising:
   activating at least one electric heater to heat said gas;
   redirecting the heated gas through the coil heat exchanger;
   introducing gaseous boil off by opening the inlet valve for a predetermined time; and for every third time the step of opening of the inlet valve is performed, opening the cooling control valve to reduce induced pressure in the coil heat exchanger; and
   raising a temperature of the sample environment to a predetermined required temperature by heat exchange with the heated gas.

2. The method of claim 1 further comprising: providing the at least one electric heater between a payload bay of the cryoprocessor and an inner wall of an insulating shell of the cryoprocessor.

3. The method of claim 1, wherein the cryogen is nitrogen; the article comprises at least one bio-sample; and wherein the step of operating the cryoprocessor in the cooling cycle comprises freezing the at least one bio-sample at controlled rates and the step of operating the cryoprocessor in the heating cycle comprises thawing the at least one bio-sample at controlled rates.

4. The method of claim 1, further comprising:
   wherein the step of operating the cryoprocessor in the heating cycle further comprises providing an additional coil on the exterior bottom of a payload of the cryoprocessor and passing the heated cryogen through the additional coil to raise the temperature of the sample environment and warm the material at a controlled rate.

5. The method of claim 1, wherein the step of constricting the inner diameter of the coil heat exchanger includes blocking the inner diameter of the coil heat exchanger with the gas, thereby preventing the cryogen to exit the cryoprocessor in a liquid phase of the cryogen.

6. The method of claim 5 further comprising wherein the pressure wave control further comprises lowering liquid requirements to cool a payload bay of the cryoprocessor.

7. The method of claim 1, wherein the pressure wave control further comprises the step of comparing a temperature of a payload of the cryoprocessor to a desired temperature and to an outlet temperature using a programmable logic controller; and wherein the heating cycle further comprises monitoring a temperature ramp rate with the programmable logic controller and when the temperature ramp rate is lower than a selected ramp rate, performing the step of introducing gaseous the boil off by opening the inlet valve for the predetermined time.

8. The method of claim 1, wherein the operating of the heating cycle further comprises engaging a PID circuit that controls timing and requirements for heat and maintains a rate of temperature rise at a desired pace.

\* \* \* \* \*